(12) United States Patent
Melsheimer

(10) Patent No.: US 7,758,565 B2
(45) Date of Patent: Jul. 20, 2010

(54) IDENTIFIABLE WIRE GUIDE

(75) Inventor: Jeffry S. Melsheimer, Springville, IN (US)

(73) Assignee: Cook Incorporated, Bloomington, IN (US)

( * ) Notice: Subject to any disclaimer, the term of this patent is extended or adjusted under 35 U.S.C. 154(b) by 296 days.

(21) Appl. No.: 11/549,481

(22) Filed: Oct. 13, 2006

(65) Prior Publication Data

US 2007/0118053 A1 May 24, 2007

Related U.S. Application Data

(60) Provisional application No. 60/727,816, filed on Oct. 18, 2005.

(51) Int. Cl.
*A61M 25/00* (2006.01)
*A61B 5/00* (2006.01)

(52) U.S. Cl. ...................... 604/528; 600/585

(58) Field of Classification Search ................ 604/528
See application file for complete search history.

(56) References Cited

U.S. PATENT DOCUMENTS

| | | |
|---|---|---|
| 2,657,691 A | 11/1953 | Nordstrom, Jr. |
| 3,521,620 A | 7/1970 | Cook |
| 3,547,103 A | 12/1970 | Cook |
| 3,656,680 A | 4/1972 | Nomura |
| 3,739,784 A | 6/1973 | Itoh |
| 3,890,997 A | 6/1975 | Wilson |
| 4,548,206 A | 10/1985 | Osborne |
| 4,569,347 A | 2/1986 | Frisbie |
| 4,601,713 A | 7/1986 | Fuqua |
| 4,650,472 A | 3/1987 | Bates |
| 4,665,906 A | 5/1987 | Jervis |
| 4,824,435 A | 4/1989 | Giesy et al. |
| 4,921,483 A | 5/1990 | Wijay et al. |
| 4,925,445 A | 5/1990 | Sakamoto et al. |
| 4,934,380 A | 6/1990 | De Toledo |
| 4,984,581 A | 1/1991 | Stice |
| 5,003,990 A | 4/1991 | Osypka |
| 5,069,226 A | 12/1991 | Yamauchi et al. |
| 5,105,818 A | 4/1992 | Christian et al. |
| 5,129,890 A | 7/1992 | Bates et al. |
| 5,131,407 A | 7/1992 | Ischinger et al. |

(Continued)

FOREIGN PATENT DOCUMENTS

EP 0 436 303 A1 10/1991

(Continued)

OTHER PUBLICATIONS

International Search Report & Written Opinion (Jan. 3, 2008).

(Continued)

*Primary Examiner*—Nicholas D Lucchesi
*Assistant Examiner*—Jason Flick
(74) *Attorney, Agent, or Firm*—Brinks Hofer Gilson & Lione

(57) ABSTRACT

A wire guide includes identification features for distinguishing between other introduced wire guides. The wire guide includes a main body having a proximal portion. An identification section is formed at the proximal portion and includes a marker for identifying the wire guide. Preferably, the marker is a surface that can be identified visually, tactilely or visually and tactilely.

19 Claims, 5 Drawing Sheets

U.S. PATENT DOCUMENTS

| | | | |
|---|---|---|---|
| 5,159,861 A | 11/1992 | Anderson | |
| 5,213,111 A | 5/1993 | Cook et al. | |
| 5,234,003 A | 8/1993 | Hall | |
| 5,242,759 A | 9/1993 | Hall | |
| 5,243,996 A | 9/1993 | Hall | |
| 5,251,640 A | 10/1993 | Osborne | |
| 5,267,958 A | 12/1993 | Buchbinder et al. | |
| 5,306,261 A | 4/1994 | Alliger et al. | |
| 5,318,527 A | 6/1994 | Hyde et al. | |
| 5,325,746 A | 7/1994 | Anderson | |
| 5,328,472 A | 7/1994 | Steinke et al. | |
| 5,328,480 A | 7/1994 | Milker et al. | |
| 5,344,413 A | 9/1994 | Allman et al. | |
| 5,354,257 A | 10/1994 | Roubin et al. | |
| 5,383,853 A | 1/1995 | Jung et al. | |
| 5,402,799 A | 4/1995 | Colon et al. | |
| 5,449,362 A | 9/1995 | Chaisson et al. | |
| 5,456,680 A | 10/1995 | Taylor et al. | |
| 5,488,959 A | 2/1996 | Ales | |
| 5,597,378 A | 1/1997 | Jervis | |
| 5,667,521 A | 9/1997 | Keown | |
| 5,738,667 A | 4/1998 | Solar | |
| 5,762,070 A | 6/1998 | Nagamatsu | |
| 5,776,079 A | 7/1998 | Cope et al. | |
| 5,776,100 A | 7/1998 | Forman | |
| 5,797,857 A | 8/1998 | Obitsu | |
| 5,810,876 A | 9/1998 | Kelleher | |
| 5,827,225 A | 10/1998 | Ma Schwab | |
| 5,873,842 A | 2/1999 | Brennen et al. | |
| 5,882,333 A | 3/1999 | Schaer et al. | |
| 5,891,056 A | 4/1999 | Ramzipour | |
| 5,893,868 A | 4/1999 | Hanson et al. | |
| 5,993,424 A | 11/1999 | Lorenzo et al. | |
| 5,997,526 A | 12/1999 | Giba et al. | |
| 6,007,517 A | 12/1999 | Anderson | |
| 6,139,510 A | 10/2000 | Palermo | |
| 6,217,567 B1 | 4/2001 | Zadno-Azizi et al. | |
| 6,221,066 B1 | 4/2001 | Ferrera et al. | |
| 6,248,092 B1 * | 6/2001 | Miraki et al. | 604/96.01 |
| 6,254,549 B1 | 7/2001 | Ramzipoor | |
| 6,254,550 B1 | 7/2001 | McNamara et al. | |
| 6,290,693 B1 | 9/2001 | Jung, Jr. et al. | |
| 6,306,141 B1 | 10/2001 | Jervis | |
| 6,309,404 B1 | 10/2001 | Krzyzanowski | |
| 6,348,041 B1 | 2/2002 | Klint | |
| 6,348,045 B1 * | 2/2002 | Malonek et al. | 604/270 |
| 6,383,146 B1 | 5/2002 | Klint | |
| 6,471,697 B1 | 10/2002 | Lesh | |
| 6,475,167 B1 | 11/2002 | Fleming et al. | |
| 6,500,130 B2 | 12/2002 | Kinsella et al. | |
| 6,502,606 B2 * | 1/2003 | Klint | 140/71 R |
| 6,517,518 B2 | 2/2003 | Nash et al. | |
| 6,530,899 B1 | 3/2003 | Savage | |
| 6,569,151 B1 | 5/2003 | Nash et al. | |
| 6,596,963 B2 | 7/2003 | Kelly | |
| 6,605,049 B1 * | 8/2003 | Wagner et al. | 600/585 |
| 6,613,002 B1 * | 9/2003 | Clark et al. | 600/593 |
| 6,638,372 B1 | 10/2003 | Abrams et al. | |
| 6,682,608 B2 | 1/2004 | Abrams et al. | |
| 6,805,676 B2 | 10/2004 | Klint | |
| 6,872,192 B2 | 3/2005 | Nash et al. | |
| 7,074,197 B2 * | 7/2006 | Reynolds et al. | 600/585 |
| 7,076,285 B2 | 7/2006 | Windheuser et al. | |
| 7,229,431 B2 | 6/2007 | Houser et al. | |
| 2002/0058888 A1 | 5/2002 | Biagtan et al. | |
| 2002/0169457 A1 | 11/2002 | Quinn | |
| 2003/0028127 A1 | 2/2003 | Balzum et al. | |
| 2003/0120208 A1 | 6/2003 | Houser et al. | |
| 2004/0073108 A1 | 4/2004 | Saeed et al. | |
| 2004/0116957 A1 | 6/2004 | Nishide | |
| 2004/0199087 A1 | 10/2004 | Swain et al. | |
| 2004/0215208 A1 | 10/2004 | Foushee et al. | |
| 2005/0027212 A1 | 2/2005 | Segner et al. | |
| 2005/0075647 A1 | 4/2005 | Walters et al. | |
| 2005/0143770 A1 | 6/2005 | Carter et al. | |
| 2005/0148902 A1 * | 7/2005 | Minar et al. | 600/585 |
| 2005/0197663 A1 | 9/2005 | Soma et al. | |
| 2005/0209533 A1 | 9/2005 | Lorenz | |
| 2006/0100544 A1 | 5/2006 | Ayala et al. | |
| 2006/0100545 A1 | 5/2006 | Ayala et al. | |
| 2007/0060908 A1 | 3/2007 | Webster et al. | |
| 2007/0167065 A1 | 7/2007 | Melsheimer et al. | |
| 2007/0185414 A1 | 8/2007 | Urbanski et al. | |
| 2007/0191790 A1 | 8/2007 | Eells et al. | |

FOREIGN PATENT DOCUMENTS

| | | |
|---|---|---|
| EP | 0829269 A1 | 3/1998 |
| EP | 1057500 A1 | 12/2000 |
| EP | 1 428 546 A2 | 6/2004 |
| WO | WO 93/14805 | 8/1993 |
| WO | WO 96/10436 | 4/1996 |
| WO | WO 99/44510 | 9/1999 |
| WO | WO 00/74565 A1 | 12/2000 |
| WO | WO 01/03764 A1 | 1/2001 |
| WO | WO 02/094364 A2 | 11/2002 |
| WO | WO2004/033016 | 4/2004 |
| WO | WO 2004/049970 A2 | 6/2004 |
| WO | WO 2004/050161 A1 | 6/2004 |
| WO | WO 2005/011530 A1 | 2/2005 |
| WO | WO 2005/011788 A1 | 2/2005 |
| WO | WO 2005/025660 A1 | 3/2005 |
| WO | WO 2005/089852 A1 | 9/2005 |
| WO | WO 2006/039216 A2 | 4/2006 |
| WO | WO 2007/084474 A1 | 7/2007 |
| WO | WO 2007/089891 A1 | 8/2007 |
| WO | WO 2007/089893 A1 | 8/2007 |

OTHER PUBLICATIONS

Notification of Transmittal of International Preliminary Report on Patentability (Jan. 10, 2008).

The Journal of Invasive Cardiology entitled "Use of a Second Buddy Wire During Percutaneous Coronary Interventions: A Simple Solution for Some Challenging Situations" dated Apr. 25, 2005, pp. 1-8.

The Journal of Invasive Cardiology entitled "Use of a Second Buddy Wire During Percutaneous Coronary Interventions: A Simple Solution for Some Challenging Situations" dated Apr. 25, 2005, pp. 1-8.

Office Action dated Mar. 17, 2008 U.S. Appl. No. 11/706,548 issued in related application.

Office Action dated Apr. 7, 2008 U.S. Appl. No. 11/699,174 issued in related application.

Office Action dated May 16, 2008 U.S. Appl. No. 11/763,355 issued in related application.

Office Action dated May 30, 2008 U.S. Appl. No. 11/507,805 issued in related application.

Office Action dated May 23, 2008 U.S. Appl. No. 11/652,430 issued in related application.

International Search Report—PCT/US2007/04827 & Opinion (Mar. 14, 2008).

Suppl) Notification of Transmittal of International Preliminary Report on Patentability—PCT/US2007/002743—(Jun. 3, 2008).

Office Action Restriction dated Mar. 3, 2008 U.S. Appl. No. 11/507,805 issued in related application.

Office Action Restriction dated Jul. 2, 2008 U.S. Appl. No. 11/699,171 issued in related application.

International Search Report/Written Opinion—PCT/US2006/040843 (Feb. 7, 2007).

International Preliminary Report on Patentability—PCT/US2007/002741 (Jun. 25, 2008).

International Search Report—PCT/US2006/040843 (Jan. 31, 2007).
International Search Report—PCT/US2007/002743 (Jun. 14, 2007).
International Search Report—PCT/US2007/002741 (Jul. 9, 2007).
International Search Report—PCT/US2006/042184 (Mar. 1, 2007).
International Search Report—PCT/US2007/001066 (Jun. 18, 2007).

International Search Report and Written Opinion—PCT/US2007/004827 (Oct. 26, 2007).

Office Action dated Nov. 15, 2007 issued in related U.S. Appl. No. 11/652,430.

Office Action dated Oct. 28, 2008 U.S. Appl. No. 11/507,805 issued in co-pending application.

Office Action dated Nov. 20, 2008 U.S. Appl. No. 11/763,355 issued in co-pending application.

Office Action dated Nov. 21, 2008 U.S. Appl. No. 11/549,473 issued in co-pending application.

Office Action dated Nov. 21, 2008 U.S. Appl. No. 11/699,171 issued in co-pending application.

Office Action dated Dec. 11, 2008 U.S. Appl. No. 11/652,430 issued in co-pending application.

Advisory Action dated Jan. 16, 2009 U.S. Appl. No. 11/507,805 issued in co-pending application.

International Preliminary Report on Patentability and Written Opinion (Jul. 24, 2008) PCT/US2007/001066.

Office Action dated Sep. 26, 2008 U.S. Appl. No. 11/706,548 issued in related application.

Office Action dated Oct. 7, 2008 U.S. Appl. No. 11/507,993 issued in related application.

Office Action dated Oct. 15, 2008 U.S. Appl. No. 11/699,174 issued in related application.

Advisory Action dated Mar. 6, 2009 U.S. Appl. No. 11/652,430 issued in co-pending application.

Office Action dated Mar. 3, 2009 U.S. Appl. No. 11/699,174 issued in co-pending application.

Office Action dated Apr. 1, 2009 U.S. Appl. No. 11/507,805 issued in co-pending application.

Office Action dated Apr. 7, 2009 U.S. Appl. No. 11/706,548 issued in co-pending application.

Office Action dated May 8, 2009 U.S. Appl. No. 11/699,171 issued in co-pending application.

Office Action dated May 14, 2009 U.S. Appl. No. 11/507,993 issued in coo-pending application.

* cited by examiner

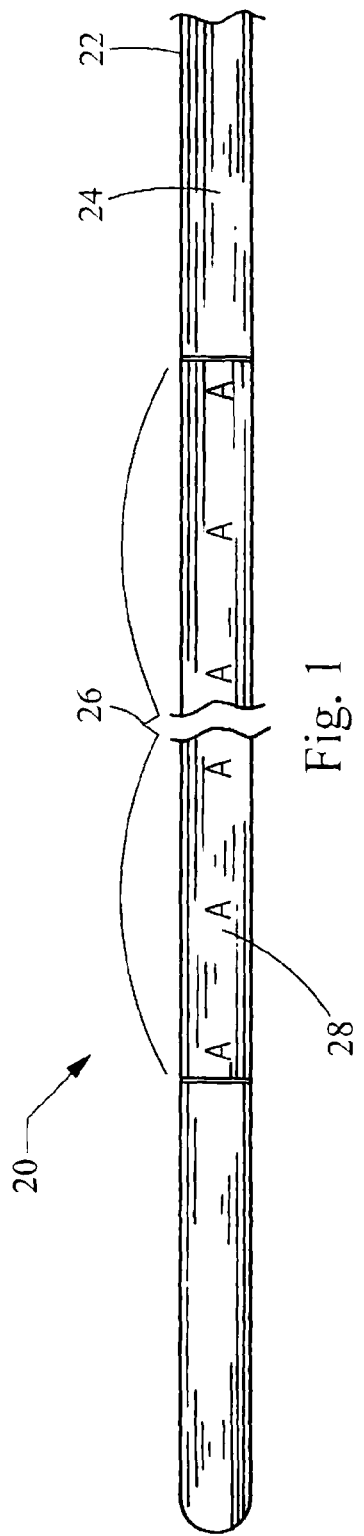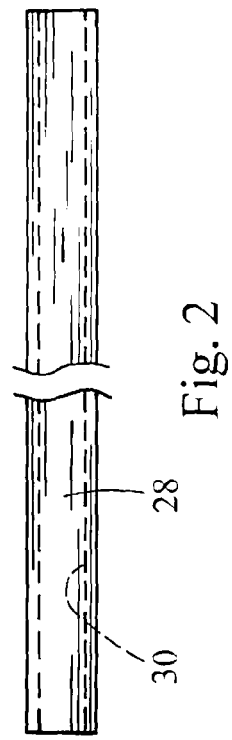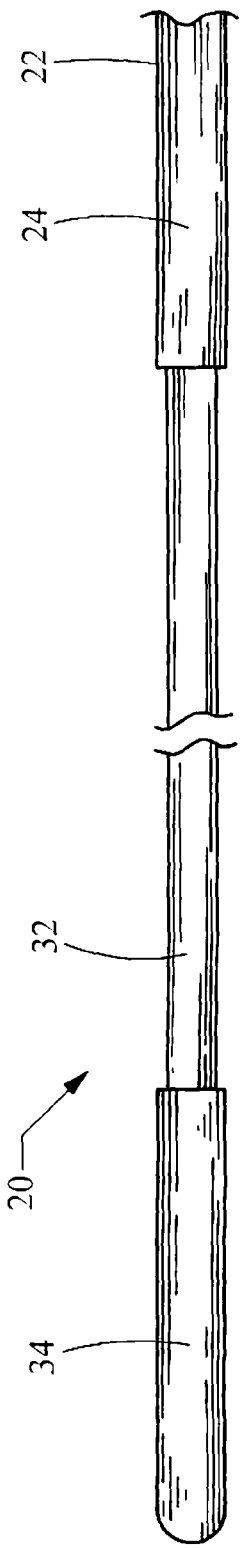

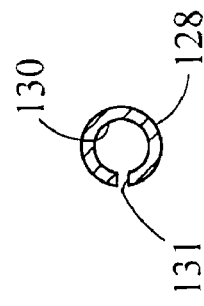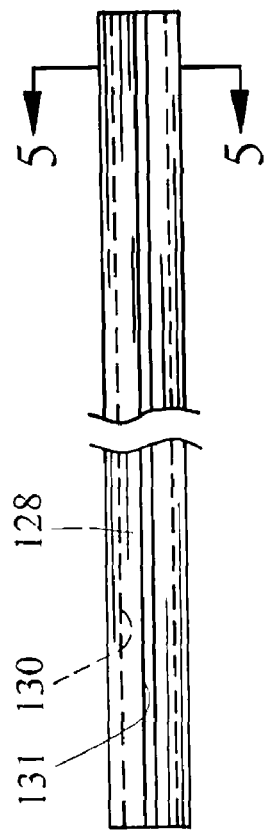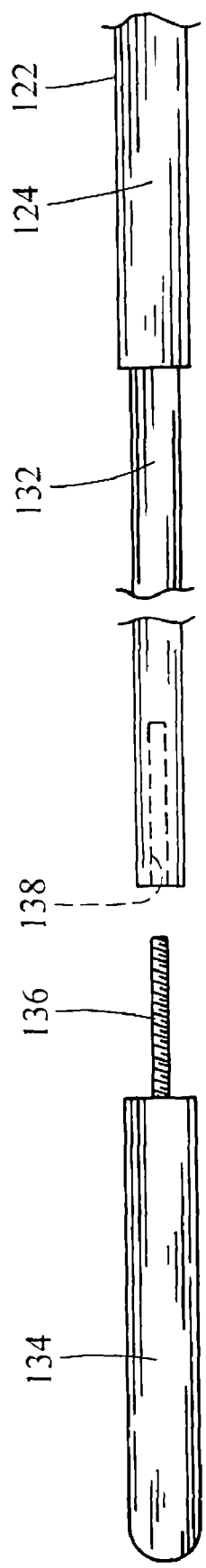

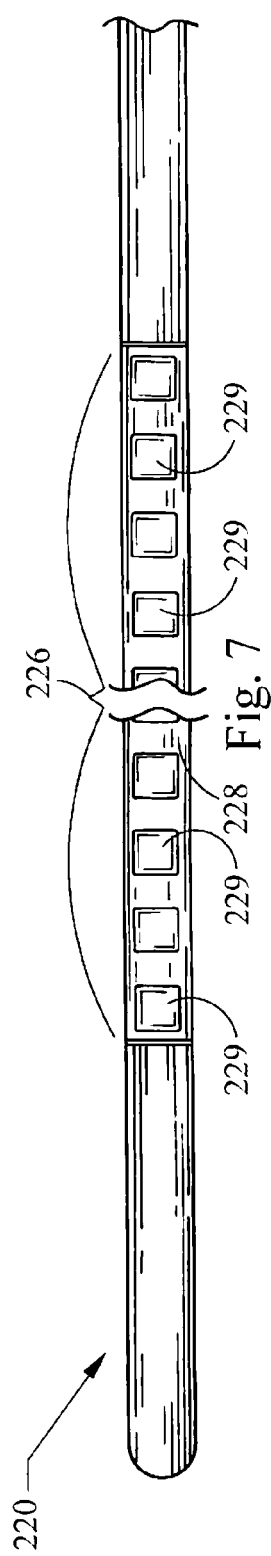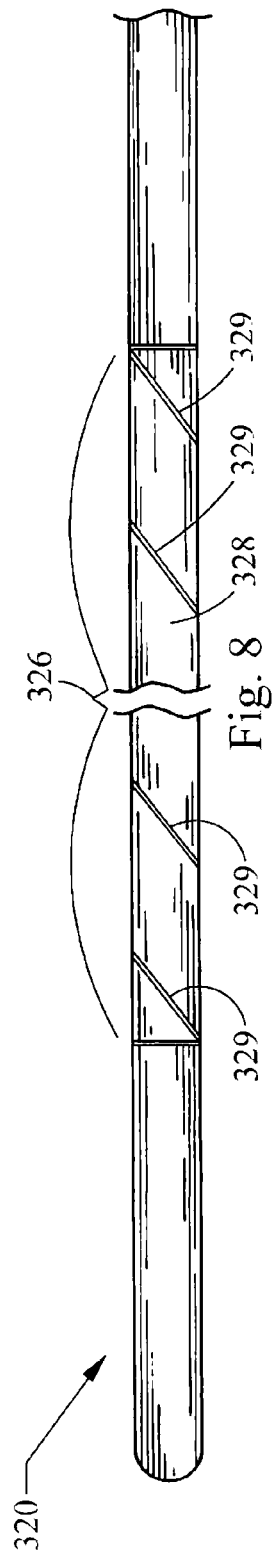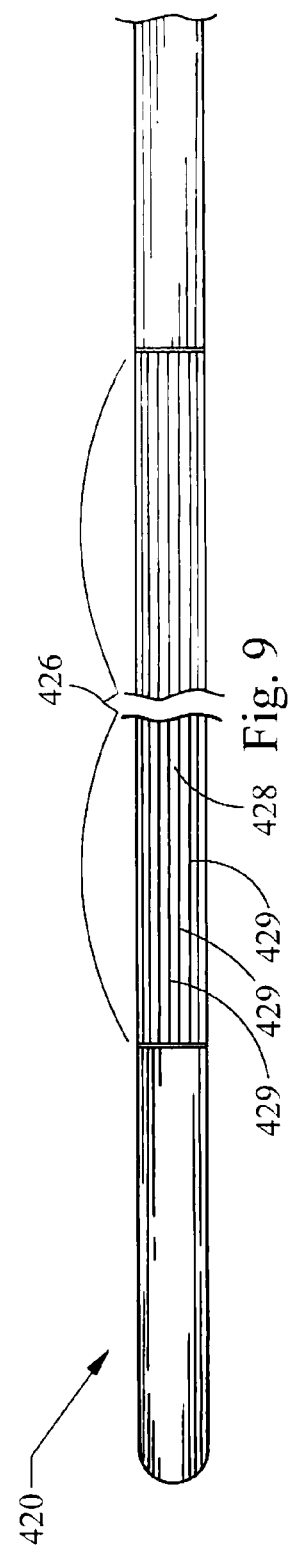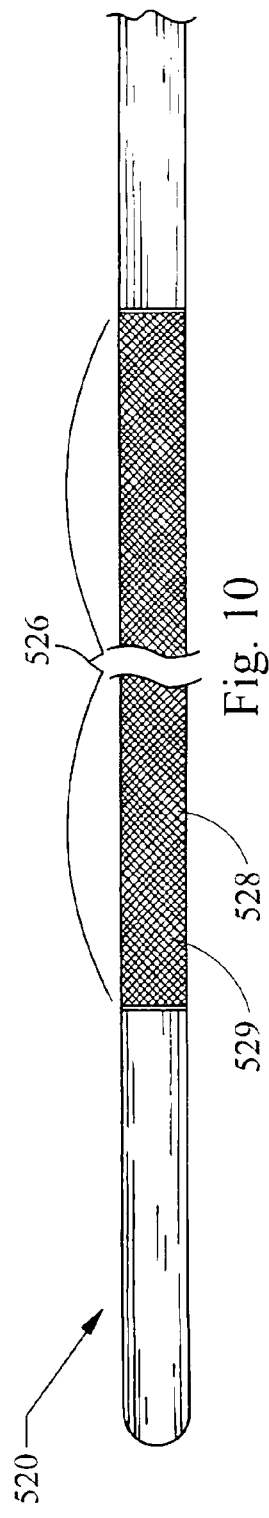

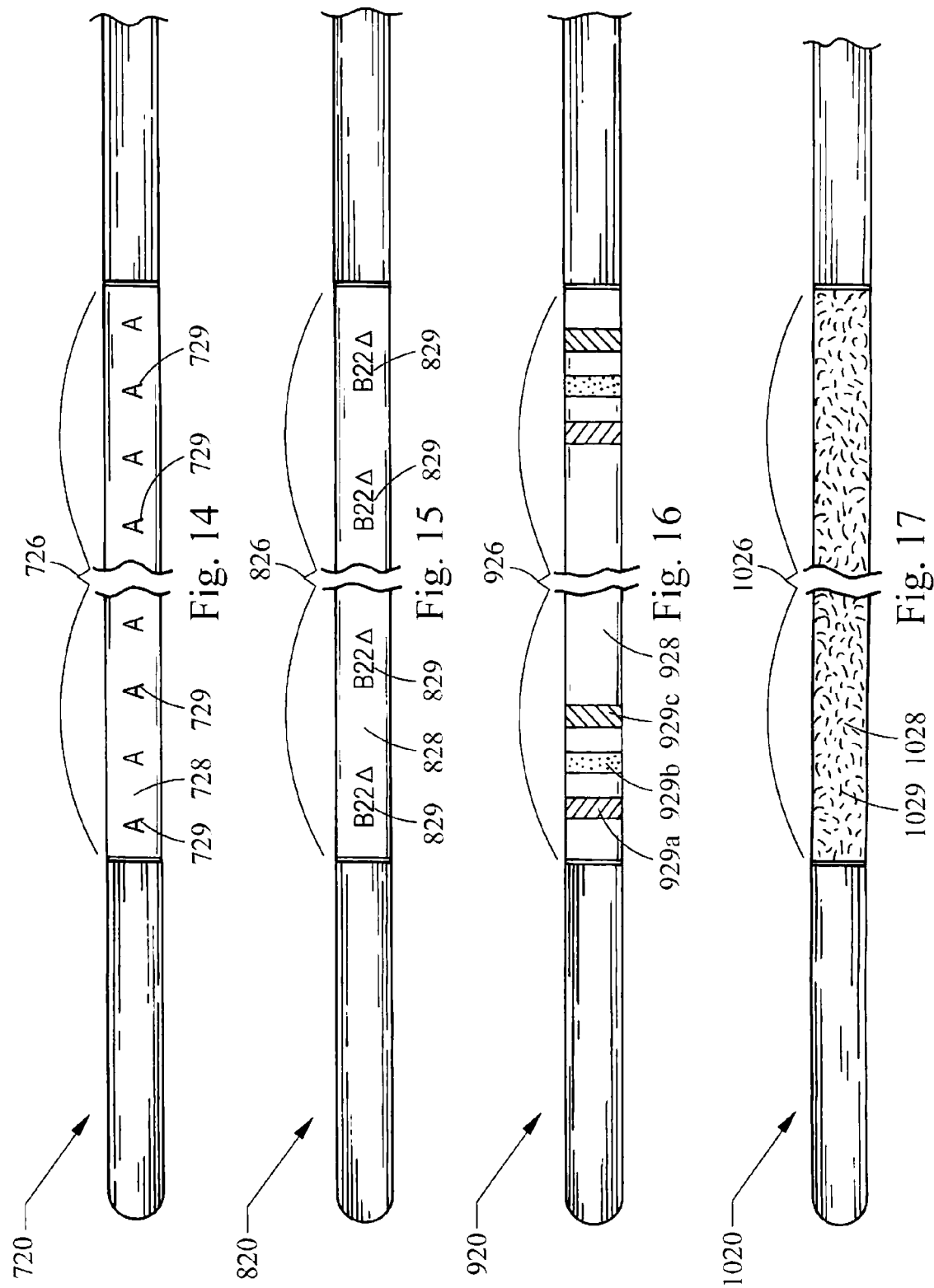

IDENTIFIABLE WIRE GUIDE

CROSS-REFERENCE TO RELATED APPLICATIONS

This application claims the benefit of U.S. Provisional Application Ser. No. 60/727,816 filed on Oct. 18, 2005, entitled "IDENTIFIABLE WIRE GUIDE", the entire contents of which are incorporated herein by reference.

FIELD OF THE INVENTION

This invention relates generally to a wire guide for use in intracorporeal procedures, and more particularly relates to the construction of a wire guide to be used in conjunction with other wire guides, such as the use of multiple wire guides for assistance during interventional procedures in vessels with proximal tortuosity, or as a more substantial wire guide for angioplasty procedures, stenting procedures, and other device placement procedures and their related devices.

BACKGROUND OF THE INVENTION

Proximal tortuosity of the vasculature is problematic for all medical catheter devices such as atherectomy devices, angioplasty devices, stent delivery devices, and filter delivery devices. Wire guides are therefore typically used to navigate the vasculature of a patient during percutaneous interventional procedures. Once the wire guide has been introduced, it may then be used to introduce one or more medical catheter devices. Thus, most wire guides are typically 0.014 inches in diameter and have a lubricious coating to enhance wire guide introduction movement. Conventional 0.014 inch floppy wire guides must have sufficient flexibility and torque control for navigation through tortuous vessels. At the same time, the wire guide must have a certain amount of rigidity to pass through lesions, straighten extremely tortuous vessels, and support medical catheter devices that are introduced over the wire guide.

Accordingly, wire guides are subjected to potentially conflicting requirements. Conventional 0.014 inch floppy wire guides are usually sufficient for navigation of moderately tortuous vessels. However, in some situations the wire guide tip may prolapse away from the site to which it is guiding the device. For example, balloon angioplasty in vessels with proximal tortuosity has been associated with a higher incidence of acute complications and procedural failure due to the inability to cross lesions with a conventional floppy wire guide, and due to the inability of the wire guide to provide adequate support to the balloon catheter. Heavy-duty wire guides, on the other hand, are generally not well suited as primary wire guides because of their stiffness and potential for causing injury to the vessel during introduction.

It may therefore be desirable to use conventional floppy wire guides for navigation of tortuous vessels, and then enhance the conventional wire guide with a supplemental wire guide. The supplemental wire guide will straighten out the vessel curves and ease further wire guide movement. Additionally, the supplemental wire guide provides greater support and enhances the tracking of balloons, stents, stent delivery devices, atherectomy devices, and other medical catheter devices as compared to a conventional floppy wire guide. This technique is commonly referred to as the "Buddy Wire" technique, details of which are disclosed in U.S. patent application Ser. No. 11/081,146, filed Mar. 16, 2005.

The applicant has discovered that it can become difficult to distinguish between the previously introduced wire guide and the supplemental wire guide (or guides), especially once the supplemental wire guide is fully advanced and positioned similarly or adjacent to the previously introduced wire guide. That is, the proximal end of these wire guides, which remains outside of the vasculature and accessible to the physician, can become confused. Multiple exchanges of wire guides during interventional procedures may further complicate wire guide identification.

Accordingly, there exists a need to provide a wire guide for intracorporeal procedures that may be easily and reliably distinguished from other introduced wire guides.

BRIEF SUMMARY OF THE INVENTION

The present invention provides a wire guide for intracorporeal procedures that may be easily and reliably distinguished from other introduced wire guides. One embodiment of the wire guide constructed in accordance with the teachings of the present invention comprises a main body having a proximal portion. An identification section is formed at the proximal portion and includes a marker for identifying the wire guide. Preferably, the marker is a surface that can be identified visually, tactilely or both visually and tactilely. For example, the surface may be treated to include a color, indicia, or a texture. The marker is preferably a sleeve disposed over the identification section, and the proximal portion may have a reduced diameter in the identification section to correspond with the sleeve. The proximal portion of the main body may be a solid or tubular mandrel, or alternatively may comprise a wound wire wherein the identification section is formed by a second wire having a diameter less than the wound wire. The sleeve has an outer diameter of substantially the same size as the outer diameter of the surrounding proximal portion of the main body. The sleeve may be constructed of a heat shrinkable plastic attached to the identification section.

An alternative embodiment of the sleeve includes a resilient tubular member having a slot through which the sleeve may be attached to the identification section. Still further, the main body may include a proximal end that is removably attached to the proximal portion adjacent the identification section. The proximal end may be removed and then replaced for attachment of a solid tubular sleeve for connecting the sleeve.

In each embodiment, the sleeve provides a surface that can be treated to include a color or indicia, such as through staining, dying, printing, painting, electrochemically marking or photolithography. The surface may also be texturized by processes such as media blasting, grinding, etching, turning, milling or knurling. Preferably, a kit of wire guides is provided containing a plurality of wire guides each having a marker such as the aforementioned sleeve, wherein each marker is distinguishable from the other markers.

BRIEF DESCRIPTION OF THE DRAWINGS

The accompanying drawings incorporated in and forming a part of the specification illustrate several aspects of the present invention, and together with the description serve to explain the principles of the invention. In the drawings:

FIG. 1 is a partial side view of the proximal end of a wire guide constructed in accordance with the teachings of the present invention;

FIG. 2 is a side view of a sleeve forming a portion of the wire guide depicted in FIG. 1;

FIG. 3 is a partial side view of the proximal end of a main body forming a portion of the wire guide depicted in FIG. 1;

FIG. 4 is a partial side view of an alternate embodiment of the wire guide depicted in FIG. 1;

FIG. 5 is a side view of an alternate embodiment of the sleeve depicted in FIG. 2;

FIG. 6 is an end view of the sleeve depicted in FIG. 5;

FIGS. 7, 8, 9 and 10 depict various alternate embodiments of the wire guide depicted in FIG. 1 illustrating different identification sleeves;

FIGS. 14-17 depict various alternate embodiments of the wire guide depicted in FIG. 1 illustrating different identification sections.

DETAILED DESCRIPTION OF THE INVENTION

Figure 11:
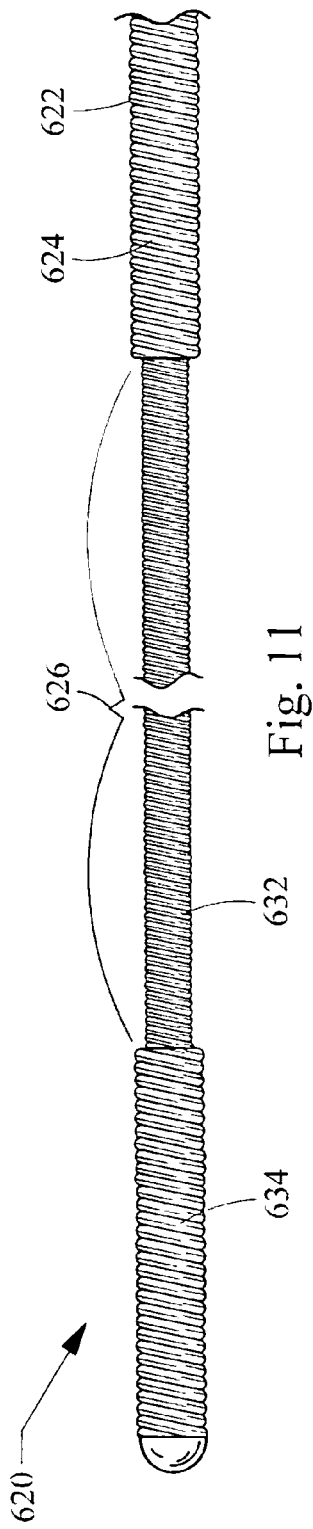
FIG. 11 is a partial side view of another alternate embodiment of the wire guide depicted in FIG. 1.

Turning now to the figures, FIGS. 1-3 depict a wire guide 20 constructed in accordance with the teachings of the present invention. Generally, the wire guide 20 includes a main body 22 having a proximal portion 24 that has been depicted in the figures. The main body 22 preferably comprises a solid mandrel, although a tubular mandrel may also be employed. The proximal portion 24 includes an identification section 26 used for identifying the wire guide 20 or otherwise distinguishing the wire guide 20 from other wire guides. To provide this identification function, a unique marker is utilized, shown here as a sleeve 28. The sleeve 28 generally comprises a tubular member defining an internal passageway 30. The passageway 30 is sized to fit over the proximal portion 24, and in particular over a reduced diameter area 32 of the identification section 26. The proximal end 34 of the main body 22 has a diameter corresponding to the remainder of the proximal portion 24.

In the embodiment depicted in FIGS. 1-3, the sleeve 28 is preferably comprised of a heat shrinkable plastic which may simply be aligned with the reduced diameter 32 of the identification section 26 and heated to interconnect the sleeve 28 and main body 22, as shown in FIG. 1. The sleeve 28 provides unique identification of the wire guide 20, and preferably includes a surface that can be identified visually, tactilely or both visually and tactilely. For example, the sleeve 28 may include indicia such as letters (e.g., A B C), numbers (e.g., 1 2 3), symbols (e.g., shapes) or combinations thereof to identify the wire guide 20, as shown in FIGS. 14 and 15. Alternatively, the sleeve 28 may include a color over all or part of the sleeve such as is shown in FIGS. 16 and 17. Further the sleeve 28 may include a texture that can be differentiated through physically touching the identification section 26, such as is shown in FIGS. 7-10. These markers will be discussed in more detail later herein.

The sleeve 28 may alternatively be formed of a non-heat shrinkable material, and preferably a more rigid material such as a metal or alloy corresponding to the wire guide 20 such as stainless steel or Nitinol (Ni—Ti), although a hard plastic or any other relatively rigid material may be used. To employ a more rigid sleeve 28, an alternate embodiment of the wire guide 120 can be used, which has been shown in FIG. 4. Here, the proximal end 134 may be selectively removed or attached to the proximal portion 124 of the main body 122, and specifically to the identification section 126 and its reduced diameter portion 132. As shown, the proximal end 134 may include a threaded male coupling 136 corresponding to a threaded female coupling 138 formed in the reduced diameter area 132. While a threaded fastener 136, 138 has been depicted in the embodiment of FIG. 4, it will be recognized by those skilled in art that numerous connection mechanisms may be employed, such as clasps, spring biased latches, quick connect mechanisms, friction fittings and the like. Accordingly, the wire guide 120 permits the sleeve 28 to be selectively attached to the identification section 126 of the proximal wire guide portion 124.

A related embodiment of the sleeve 128 has been depicted in FIGS. 5 and 6 for use with the embodiment shown in FIG. 3. Here, the sleeve 128 may again be formed of a non-heat shrinkable material, and preferably a resilient material corresponding to the material of the wire guide as in the embodiment discussed above. The sleeve 128 again comprises a tubular structure defining an inner passageway 130 sized to receive the reduced diameter 32 of proximal portion 24 in the identification area 26. In this embodiment, however, the sleeve 128 includes a slot 131, whereby the diameter of the sleeve 128 and the size of the slot 131 may be adjusted due to the resiliency of the sleeve material. In this manner, the sleeve 128 may be selectively connected or disconnected to the identification section 26 of the wire guide 20, by passing slot 131 over reduced diameter 32, thereby eliminating the need for a removable proximal end 134 as shown in FIG. 4.

In all the aforementioned embodiments, it can be seen that the identification section 26, 126, and particularly the sleeve 28, 128, may be provided with a virtually unlimited number of unique markers that can serve to identify the wire guide 20, 120 and distinguish it from other wire guides. For example, FIG. 7 depicts a wire guide 220 having an identification section 226 with a sleeve 228 that includes a plurality of dimples or depressions 229. While square depressions 229 have been, illustrated, depressions 229 may be of any shape or size. FIG. 8 depicts a wire guide 320 having an identification section 326 with a sleeve 328 including an angled groove 329 (angled relative to the longitudinal axis of the wire guide 320). It will be recognized that groove 329 may be a series of grooves or alternatively may be a single groove formed in a helical path along the sleeve 328. FIG. 9 depicts a wire guide 420 having an identification section 426 with a sleeve 428 having a series of longitudinally extending grooves 429. FIG. 10 depicts a wire guide 520 having an identification section 526 with a sleeve 528 having knurled outer surface 529, which may alternately be formed by grooves going in two different directions. FIG. 14 depicts a wire guide 720 having an identification section 726 with a sleeve 728 having indicia 729, namely letters "A". It can be printed on the sleeve 728, or otherwise formed directly into the sleeve 728 through a manufacturing method described below. FIG. 15 depicts a wire guide 820 having an identification section 826 with a sleeve 828 having multiple forms of indicia, namely "B22▲", intended to have a meaning related to the wire guide 820 such as the "B" wire of size 0.022 inches and a triangle denoting a particular wire guide type. FIG. 16 depicts a wire guide 920 having an identification section 926 with a sleeve 928 having bands of color 929a, 929b, 929c. Each of these colored bands 929a, 929b, 929c may be of the same color or different colors (as depicted) and likewise may include any number of bands of any size. Finally, FIG. 17 depicts a wire guide 1020 having an identification section 1026 with a sleeve 1028 formed entirely of a single color 1029.

Accordingly, it will be seen by those skilled in the art that the surface of the sleeve 28 may include indicia or texture formed by media blasting, grinding, etching, turning, milling or knurling. Likewise, the sleeve 28 may include indicia or color formed by either staining, dying, printing, painting, electrochemically marking, or photolithography. The present invention encompasses any now known or future developed method for providing a visually sensed or a tactilely sensed marker that can serve as an identification of the wire guide 20. It will also be recognized that the sleeve 28, 128 may be eliminated, and the identifiable markers may be directly formed on the outer surface of the wire guide 20, 120.

It will also be recognized that a kit of wire guides may be provided. Preferably, the kit includes a plurality of wire guides 20, 120, 220, 320, 420, 520, 720, 820, 920, 1020 each having an identification section including a marker distinguishable from the other markers, such as the sleeves 28, 128, 228, 328, 428, 528, 728, 828, 928, 1028 depicted in the figures. Supplemental sleeves may also be provided, whereby the medical professional can customize a set of wire guides to be used. In this manner, the wire guides and their identification markers can correspond to the preferences of the medical professional.

Figure 12:
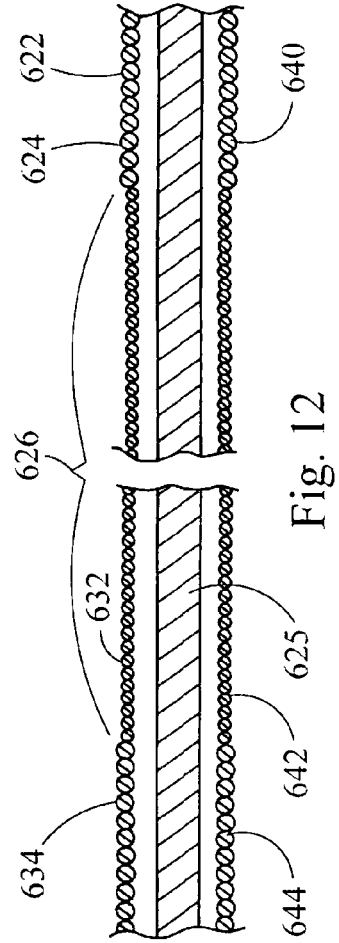
FIG. 12 is an enlarged sectional view of the wire guide depicted in FIG. 11.

In the above-described embodiments, the main body of the wire guide has been depicted as a solid mandrel. However, in the embodiment depicted in FIGS. 11 and 12, a wire guide 620 includes a main body 622 and proximal portion 624 that is formed out of a wound wire 640. The wire 640 is wound around a safety wire 625 which extends longitudinally through the interior of wire guide 620. As with the prior embodiments, the proximal portion 624 includes an identification section 626 having a reduced diameter area 632. A proximal end 634 has a diameter similar to the remainder of the main body 622. In order to form the reduced diameter area 632, a second wire has been used to form this identification section 626. That is, a first wire 640 is used to form the main body 622 and in its proximal portion 624, although a second wire 642 of reduced diameter or cross-section, is spliced into the wind in order to define the reduced diameter area 632. A third wire 644 is then connected to the second wire 642 to form the proximal end 634. In this manner, the aforementioned sleeves 28, 128 may be attached to the reduced diameter area 632 to complete the identification section 626 using any of the methods or manners discussed above.

Figure 13:
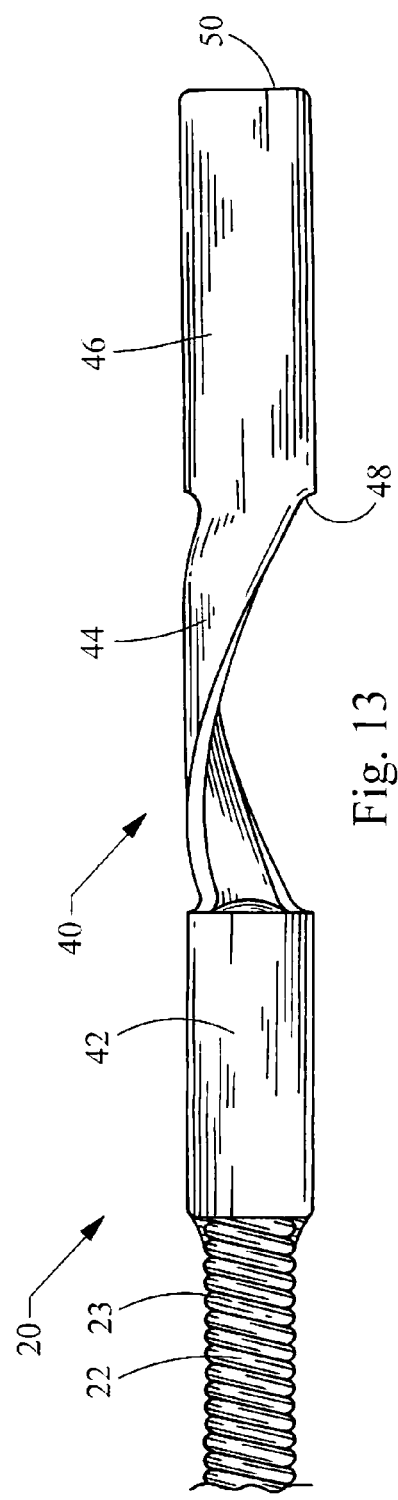
FIG. 13 is a partial side view of a distal end of the wire guide depicted in FIG. 1.

Finally, FIG. 13 depicts the wire guide 20 of FIG. 1, and more particularly a distal portion 23 of the main body 22. The distal portion 23 preferably includes a special distal tip portion 40 which is structured for coupling the wire guide 20 to a previously introduced wire guide as discussed in the Background section of the application. It will be recognized that the wire guide 20 need not include this special distal tip portion 40, and may comprise a standard proximal end portion. The distal tip portion 40 of FIG. 13 includes a first section 42 connected to the proximal portion 23, a second section 44 comprising a strip, the strip interconnecting the first section 42 to a third section 46. The third section 46 includes an internal passageway sized to receive the previously introduced wire guide, denoted by a proximal opening 48 in a distal opening 50 through which the previously introduced wire guide may pass. Further details of the depicted distal tip portion 40, as well as various other unique distal coupling structures may be found in co-pending U.S. Patent Application Nos. 60/711,102 filed Aug. 25, 2005; 60/711,261 filed Aug. 25, 2005; and Ser. No. 11/081,146, filed Mar. 16, 2005; 60/730,582 filed Oct. 27, 2005; 60/730,776 filed Oct. 27, 2005; 60/758,880 filed Jan. 13, 2006; 60/763,511 filed Jan. 31, 2006; 60/763,523 filed Jan. 31, 2006; 60/773,944 filed Feb. 16, 2006; 60/833,144 filed Jul. 25, 2006; Ser. No. 11/507,805 filed Aug. 22, 2006; Ser. No. 11/507,993 filed Aug. 22, 2006, the disclosures of which are hereby incorporated by reference in their entirety.

Notably, the identification section of the wire guides described herein are sized to be passed through the passageway of the third section 46, thereby providing easy coupling of two wire guides. Preferably, the outer diameter of the identifications sections and the sleeve are about the same size as the outer diameter of their corresponding proximal portions. In this manner, smooth and reliable coupling of two or more wire guides is readily achieved.

Accordingly, it will be recognized by those skilled in the art that the wire guide of the present invention provides simple and reliable identification of the wire guide, so that the wire guide may be readily distinguished from other introduced wire guides. The described identification section provides clear visual identification of the wire guide, while tactile markers such as a surface texture permit a medical professional to readily distinguish the wire guides without requiring a shift of visual focus. Permanent or selectively attachable sleeves provide clear identification and may be utilized by the medical professional to customize the distinguishing features of the wire guide to meet their preferences.

The foregoing description of various embodiments of the invention has been presented for purposes of illustration and description. It is not intended to be exhaustive or to limit the invention to the precise embodiments disclosed. Numerous modifications or variations are possible in light of the above teachings. For example, wire guides are often used in percutaneous interventional procedures, however it will be recognized by those skilled in the art that the wire guides of the present invention may also be employed in endoscopic or other intracorporeal procedures. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A wire guide for use in a patient's body during intracorporeal procedures, the wire guide comprising:
    a main body having a proximal portion and a distal portion, the proximal portion located proximal to the distal portion, the proximal portion defining a proximal end and the distal portion defining a distal end, the distal end being inserted into the patient's body, the proximal end remaining outside the patient's body;
    an identification section formed as part of the proximal portion of the main body and located adjacent to the proximal end having a reduced diameter; and
    a sleeve disposed over the reduced diameter of the identification section and detachable therefrom, the sleeve including a marker for identifying the wire guide and distinguishing the wire guide from other wire guides;
    wherein the sleeve has an outer diameter of substantially the same size as the outer diameter of the surrounding proximal portion of the main body.

2. The wire guide of claim 1, wherein the marker is a surface that can be identified visually or tactilely.

3. The wire guide of claim 2, wherein the surface has been treated to include at least one of a color, an indicia, or a texture.

4. The wire guide of claim 1, wherein the proximal portion of the main body is a solid or tubular mandrel.

5. The wire guide of claim 1, wherein the main body includes a proximal end removably attached to the proximal portion adjacent the identification section.

6. The wire guide of claim 1, wherein the sleeve is constructed of a heat shrinkable plastic.

7. The wire guide of claim 3, wherein the marker contains color formed by at least one of staining, dying, printing, painting, electrochemically marking or photolithography.

8. The wire guide of claim 3, wherein the marker contains texture formed by at least one of media blasting, grinding, etching, turning, milling or knurling.

9. The wire guide of claim 8, wherein the marker contains a texture that is different from the surrounding texture of the proximal portion of the main body.

10. The wire guide of claim 8, wherein the texture includes at least one of grooves, dimples, ridges, or bumps.

11. The wire guide of claim 1, wherein the main body includes a distal portion structured for coupling the wire guide to a previously introduced wire guide.

12. The wire guide of claim 11, wherein the distal portion includes a passageway sized to receive the previously introduced wire guide.

13. A wire guide for use in a patient's body during intracorporeal procedures, the wire guide comprising:
 a main body having a proximal portion and a distal portion, the proximal portion located proximal to the distal portion, the proximal portion defining a proximal end and the distal portion defining a distal end, the distal end being inserted into the patient's body, the proximal end remaining outside the patient's body; and
 an identification section formed as part of the proximal portion of the main body and located adjacent to the proximal end having a reduced diameter;
 wherein the proximal portion of the main body is a wound wire, and the identification section is formed by a second wire having a diameter smaller than the wound wire.

14. A wire guide for use in a patient's body during intracorporeal procedures, the wire guide comprising:
 a main body having a proximal portion and a distal portion, the proximal portion located proximal to the distal portion, the proximal portion defining a proximal end and the distal portion defining a distal end, the distal end being inserted into the patient's body, the proximal end remaining outside the patient's body;
 an identification section formed as part of the proximal portion of the main body and located adjacent to the proximal end; and
 a sleeve disposed over the identification section and detachable therefrom, the sleeve including a marker for identifying the wire guide and distinguishing the wire guide from other wire guides;
 wherein the sleeve is a resilient tubular member having a slot through which the sleeve may be disposed over the identification section.

15. The wire guide of claim 14, wherein the proximal portion has a reduced diameter in the identification section sized to receive the sleeve.

16. The wire guide of claim 14, wherein the sleeve has an outer diameter of substantially the same size as the outer diameter of the surrounding proximal portion of the main body.

17. A wire guide kit for use in a patient's body during intracorporeal procedures, the kit comprising:
 one or more wire guides, each wire guide comprising a main body having a proximal portion and a distal portion, the proximal portion located proximal to the distal portion, the proximal portion defining a proximal end including an identification section with a reduced diameter; and
 a plurality of sleeves, each sleeve adapted to be disposed over the reduced diameter identification section of the main body and detachable therefrom;
 wherein each sleeve includes a marker for identifying the wire guide and distinguishing the wire guide from other wire guides;
 wherein the sleeve has an outer diameter of substantially the same size as the outer diameter of the surrounding proximal portion of the main body.

18. The wire guide of claim 17, wherein each marker is a surface that can be identified visually or tactilely.

19. The wire guide of claim 18, wherein the surface has been treated to include at least one of a color, indicia, or a texture.

* * * * *